US007989507B2

(12) United States Patent
Rising

(10) Patent No.: US 7,989,507 B2
(45) Date of Patent: Aug. 2, 2011

(54) PRODUCTION OF FUEL MATERIALS UTILIZING WASTE CARBON DIOXIDE AND HYDROGEN FROM RENEWABLE RESOURCES

(75) Inventor: Bruce W. Rising, Oviedo, FL (US)

(73) Assignee: Siemens Aktiengesellschaft, Munich (DE)

( * ) Notice: Subject to any disclaimer, the term of this patent is extended or adjusted under 35 U.S.C. 154(b) by 454 days.

(21) Appl. No.: 12/123,515

(22) Filed: May 20, 2008

(65) Prior Publication Data
US 2009/0289227 A1    Nov. 26, 2009

(51) Int. Cl.
 *C07C 27/00* (2006.01)
(52) U.S. Cl. .................. 518/700; 518/702; 518/703
(58) Field of Classification Search .................. 518/700, 518/702, 703
 See application file for complete search history.

(56) References Cited

U.S. PATENT DOCUMENTS

| 2,692,274 | A | * | 10/1954 | Kolbel et al. ................. 518/706 |
| 4,810,266 | A | | 3/1989 | Zinnen et al. |
| 4,847,231 | A | | 7/1989 | Gratzel et al. |
| 5,026,934 | A | | 6/1991 | Bains et al. |
| 5,149,464 | A | | 9/1992 | Green et al. |
| 5,167,937 | A | | 12/1992 | Harandi et al. |
| 6,293,979 | B1 | | 9/2001 | Choudhary et al. |
| 6,419,888 | B1 | * | 7/2002 | Wyckoff ....................... 423/220 |
| 6,673,270 | B1 | | 1/2004 | De Jong et al. |
| 6,838,071 | B1 | | 1/2005 | Olsvik et al. |
| 2007/0244208 | A1 | * | 10/2007 | Shulenberger et al. ....... 518/726 |
| 2008/0060346 | A1 | | 3/2008 | Asen et al. |
| 2008/0072752 | A1 | | 3/2008 | Kumar |
| 2009/0235587 | A1 | * | 9/2009 | Hawkes et al. ................. 48/202 |

OTHER PUBLICATIONS

Lewis et al., Synthesis of Methanol from Carbon Monoxide and Hydrogen. Ind. Eng. Chem. 1928;20(3):285-290.
Brown et al., Methanol from Hydrogen and Carbon Monoxide. Ind. Eng. Chem. 1928; 20( 9):960-966.
Chang et al., MTG: origin, evolution operation. CHEMTECH. 1987;17(12):624-631.
Heinritz-Adrian et al., An Alternative Route from Coal to Liquids: Methanol-to-Gasoline (MTG) Technology (2007) http://www.gasification.org/Docs/2007_Papers/49HEIN.pdf.
Kobayashi et al., Novel CO2 Electrochemical Reduction to Methanol for H2 Storage, Energy & Fuels. 2004;18( 1):285-286.
Martin et al., A Concept for Producing Carbon-Neutral Synthetic Fuels and Chemicals, Los Alamos National Laboratory Public Release (LA-UR-07-7897), Nov. 2007.
Gielen, The Impact of CO2 Capture and Storage on Future Gas Use, Paper prepared for the "Global Watch Seminar," NTNU, Trondheim, Norway, Aug. 29, 2003.
Hustad et al., Review over Recent Norwegian Studies Regarding Low Cost CO2 Emission Power Plant Technology, Cairns, Australia, Paper Presentation, Aug. 13-16, 2000.
MHI to Conduct Verification Test of Flue Gas CO2 Recovery Technology at Coal-fired Power Generation Facility, http://mhi-ir.jp/english/new/sec1/20050121089, Dec. 19, 2005.
Ciferno, NETL Carbon Sequestration Program, US Perspective on CO2 Capture and Separation, Stanford University, Apr. 27, 2004.
Xu et al., Future CO2 Capture Technology for the Canadian Market, Report No. COAL R309, BERR/Pub URN 07/1251, Dept. for Business Enterprise and REgulatory Reform, Mar. 2007.
Lachowtra et al., Methanol Synthesis from Carbon Dioxide and Hydrogen over Mn-prompted Copper/Zinc/Zirconia Catalysts. React. Kinet. Catal. Lett. 2004;83(2):269-273.
Herzog et al. Carbon capture and Storage from Fossil Fuel Use, Contribution to Encyclopedia of Energy, to be published 2004, http://sequestration.mit.edu/pdf/enclyclopedia_of_energy_article.pdf.
Sung Lee et al., A comparative study of methanol synthesis from CO2/H2 and CO/H2 over a Cu/ZnO/Al3O3 catalyst. Journal of Catalysis 1993;144(2):414-424 (Abstract only).
Fujita et al., Methanol Synthesis from CO2 at Atmospheric Pressure over Cu/ZnO Catalyst: Role of Methoxide Species formed on ZnO Support. Catalysis Letter 1992;13:349-358.
Yang et al., Methanol Synthesis from CO2-rich Syngas Over a ZrO2 Doped CuZnO Catalyst. Catalysis Today. 2006;115:222-227.
Bailey et al., Post-combustion Decarbonisation Processes. Oil & Gas Science and Technology—Rev. IFP. 2005;60(3):461-474.
Reubroycharoen et al., A New Low-Temperature Methanol Synthesis from Low-Grade Syngas. Prepr. Pap.-Am. Chem. Soc., Div. Fuel Chem.. 2004;49(2):708-709.
Wu et al., Enzymatic Conversion of CO2 to Methanol: Effects of Silica Gel and ADH on Enzyme Activity. Prepr. Pap.-Am. Chem. Soc., Div. Fuel Chem., 2004;49(1):120-121.
Jitaru, Electrochemical Carbon Dioxide Reduction—Fundamental and Applied Topics (Review). J. of the Univ. of Chem. Technology and Metallurgy. 2007;42(4):333-344.
Granite, Review of Novel Methods for Carbon Dioxide Sequestration from Flue and Fuel Gases. Prepr. Pap.-Am. Chem. Soc., Div. Fuel Chem. 2004;49(1):242-244.

\* cited by examiner

*Primary Examiner* — Jafar Parsa

(57) ABSTRACT

The present invention is directed to a method for utilizing $CO_2$ waste comprising recovering carbon dioxide from an industrial process that produces a waste stream comprising carbon dioxide in an amount greater than an amount of carbon dioxide present in starting materials for the industrial process. The method further includes producing hydrogen using a renewable energy resource and producing a hydrocarbon material utilizing the produced hydrogen and the recovered carbon dioxide.

12 Claims, 3 Drawing Sheets

PRODUCTION OF FUEL MATERIALS UTILIZING WASTE CARBON DIOXIDE AND HYDROGEN FROM RENEWABLE RESOURCES

FIELD OF THE INVENTION

The present invention relates to a method and system for producing fuel materials from waste carbon dioxide using renewable resources, and more particularly to a method and system for producing fuel materials from carbon dioxide recovered from a waste stream of an industrial process and hydrogen produced using renewable energy resources.

BACKGROUND OF THE INVENTION

The need to control the world's greenhouse gases is a principle focus of the world today. Greenhouse gases, i.e. carbon dioxide, may be emitted into the atmosphere through natural processes and human activities, such as the combustion of fossil fuels (oil, natural gas, and coal), solid waste, trees and wood products, and also as a result of other chemical reactions (e.g., manufacture of cement). Carbon dioxide is a particularly critical greenhouse gas because it not only transmits visible light, but strongly absorbs energy in the infrared wavelengths at which the earth radiates energy to space. The absorbed energy may be re-radiated to the earth, thereby warming the earth. Atmospheric mixing ratios for carbon dioxide are now higher than at any time in the last 800,000 years, standing at 383 parts per million (ppm) compared to a pre-industrial revolution high of 280 ppm, although this value may vary by location and time. Currently, carbon dioxide emissions in the U.S. are at about 6 billion tons annually and 18 billion tons globally. Reducing carbon dioxide emissions from its source is one primary aim of a number of global warming protocols, however, substantial elimination of carbon dioxide production from the vast majority of CO2 emission sources is not likely to be realized.

BRIEF DESCRIPTION OF THE DRAWINGS

The invention is explained in the following description in view of the drawings that show.

DETAILED DESCRIPTION OF THE INVENTION

The inventors of the present invention have developed a novel method and system for utilizing waste carbon dioxide for the production of useful fuel materials. In one aspect of the present invention, the present invention provides a novel, efficient, and economical method and system for producing useful fuel materials, i.e. methane, methanol carbon monoxide, syngas, gasoline products, and/or other fuel materials, from carbon dioxide recovered from carbon dioxide-containing waste streams via hydrogen produced by renewable energy resources. In this way, the method and system of the present invention are capable of utilizing waste carbon dioxide to generate substantial amounts of useful fuel materials, as well as reducing the amount of carbon dioxide transmitted into the atmosphere and conserving conventional fossil fuels. As a result, the typical problems, difficulties and expense associated with carbon dioxide disposal may also be reduced or eliminated. Typical carbon disposal costs include storage costs and the cost of deep-well injection or other disposal techniques. In addition, the present invention takes advantage of the remote locations of both renewable energy power generation plants, i.e. wind farms, and carbon dioxide producing industrial plants, such as power plants. The close proximity of plants where hydrogen may be generated from renewable energy resources and plants where carbon dioxide may be captured from waste streams along with the use of materials produced by each, reduces storage and transport costs in the production of the valuable fuels according to the claimed invention.

Figure 1:
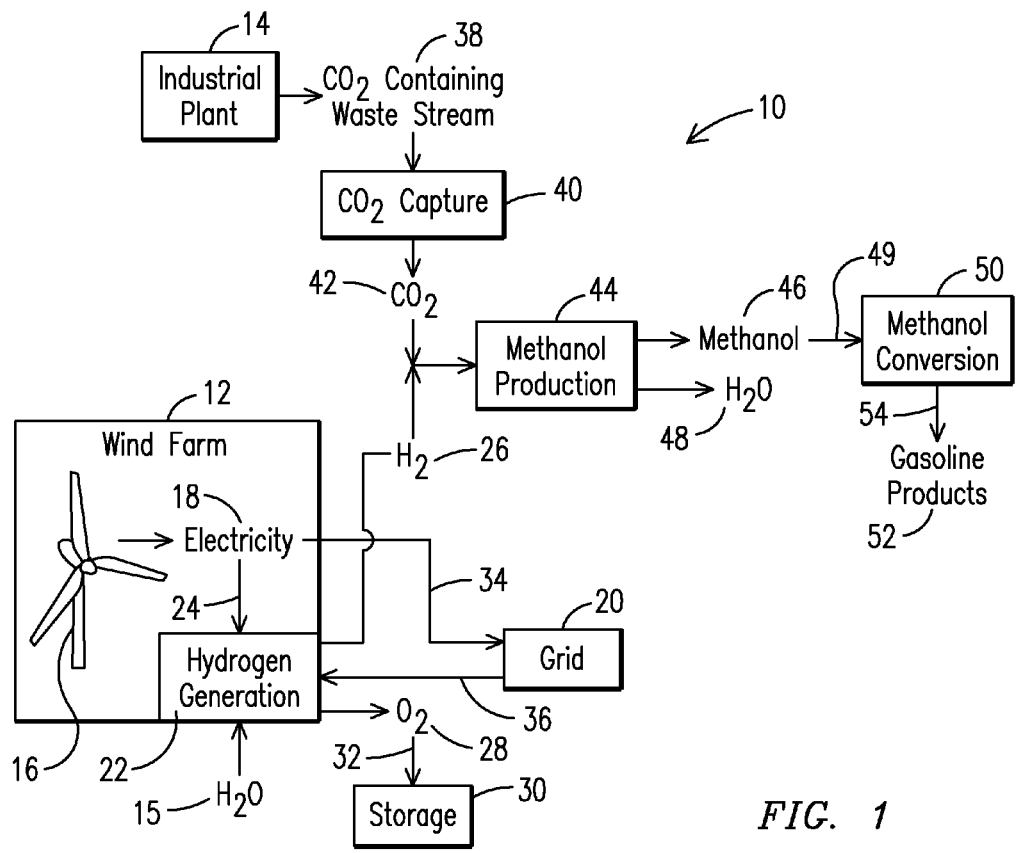
FIG. 1 is a flow schematic of a system for producing methanol and/or hydrocarbon fuels from recovered carbon dioxide and hydrogen produced from a renewable energy resource according to one embodiment of the present invention.

FIG. 1 depicts an embodiment of a system 10 for utilizing waste carbon dioxide for the production of useful fuel materials in accordance with the present invention. The system 10 includes a plant, i.e. a wind farm 12, as is known in the art, for producing energy from a renewable resource and a plant, i.e. an industrial plant 14, which produces carbon dioxide as a waste product. The wind farm 12 is typically located in a remote location, such as at high altitudes, on plains, or away from population centers, where wind speeds are likely to be relatively high and consistent on average. In an embodiment, the wind farm 12 includes a plurality of wind turbines 16, each of which converts the kinetic energy in wind into mechanical energy. The mechanical energy is then converted to electricity 18, which may be delivered to an electrical power distribution grid 20 (storage of electricity on the grid 20 is an option when such mechanisms are available). In one aspect of the present invention, at least a portion of the electricity 18 generated by the wind turbines 16 is directed to hydrogen generation 22 as indicted by arrow 24. The electricity 18 is utilized for the production of hydrogen 26 and oxygen 28 from water 15, which is delivered to an electrolytic cell as shown by arrow 17 at hydrogen generation 22. The electrolysis takes place according to the following electrolysis equation:

$$H_2O + \text{electricity} \rightarrow H_2 + \tfrac{1}{2}O_2 \qquad (I)$$

Typically, known electrolysis processes require about 60 kW-hr of energy per kilogram of hydrogen produced by the electrolysis of water. The produced hydrogen 26 may be used for the production of useful fuel materials as set forth below. In addition, per kilogram of the produced hydrogen 26, eight kilograms of oxygen 28 are also produced. The produced oxygen 28 may be fed to a storage facility 30 for storage and transport of the material from the wind farm 12 as shown by arrow 32. As such, the electrolysis reaction also provides a useful byproduct (oxygen 28) that may be used in other industrial processes such as gasification to produce CO, the production of an oxy-fuel, and/or a process that could potentially provide a source of carbon dioxide for any reaction as set forth herein.

In an embodiment, the electricity 18 produced by the wind turbines 16 may be used exclusively at hydrogen generation 22 for the production of hydrogen and oxygen. Alternatively, the electricity 18 produced by the wind farm 12 need not be utilized at all or may be only partially used at hydrogen generation 22. In this case, the electricity 18 is transferred to the grid 20 as shown by arrow 34 for storage thereon along with or instead of the transfer of the electricity 18 to hydrogen generation 22. Any electricity 18 transferred to and stored on the electrical grid 20 may be sold or acquired as needed. Along with the grid 20, the production of hydrogen 26 in hydrogen generation 22 may be performed on a consistent basis using wholly or partially a renewable energy resource. If the production of hydrogen is required, and no wind is available at any point in time, the electricity 18 produced by the wind farm 12 or other electricity stored on the grid 20 from other sources may be transferred from the grid 20 to hydrogen generation 22 to drive the electrolysis reaction as shown by arrow 36.

It is contemplated that although a wind farm is discussed herein, the wind farm 12 is merely exemplary of a renewable energy resource. Alternatively, any other suitable renewable energy resource may be used to produce power to drive the electrolysis reaction for the production of hydrogen. Other exemplary renewable energy resources include, but are not limited to sunlight, hydroelectric, rain, waves, tides, and geothermal heat, each of which may be naturally replenished.

In a next step, the hydrogen 26 produced from the wind farm 12 is combined with carbon dioxide. In an embodiment, the carbon dioxide is recovered from a waste stream of an industrial process. As is also shown in FIG. 1, the industrial plant 14 provides a process, such as an industrial process, that forms a carbon dioxide-containing waste stream 38. Numerous industrial processes are known to produce mass amounts of carbon dioxide waste. In an embodiment, the industrial plant 14 may be a power plant that includes a plurality of gas turbine combustion engines for the combustion of fuel, or any other heat engine with a carbon rich fuel supply, i.e. a coal-fired power plant. Each of these industrial plants produces a carbon dioxide-containing waste stream comprising carbon dioxide in an amount greater than an amount of carbon dioxide present in starting materials for the industrial process. Further, other industrial processes such as calcining operations, fuel decarbonization, and the like, produce relatively large quantities of carbon dioxide waste.

Typically, either a portion of the exhaust gas or waste is emptied into the atmosphere or various terrestrial and aquatic methods are used for disposing the produced carbon dioxide-containing products. The present invention provides a method for utilizing the carbon dioxide that would otherwise be emptied as waste into the atmosphere or would be required to be stored or disposed of by methods that are expensive and require storage size and space.

In an embodiment, the wind farm 12 and the power plant 14 are located in relatively close proximity to one another at a remote location. In an embodiment, the wind farm 12 has been optimized for the performance of the wind generation. In a particular embodiment, the wind farm 12 and power plant 14, for example, are located within 10 miles of one another. In this way, the transportation costs for products, i.e. carbon dioxide, useful in the production of fuel materials are kept at a minimum and are readily available to produce the desired products at a central location.

To utilize the carbon dioxide that would otherwise be disposed of in an environmentally unfriendly and/or costly manner, $CO_2$ capture 40 recovers carbon dioxide 42 in the carbon dioxide-containing waste stream 38. In an embodiment, the products of a combustion process may, for example, be passed through a condenser that condenses the majority of gases in the exhaust gas, i.e. steam. The gases exiting the condenser may comprise carbon dioxide and can be directed out of the condenser. The carbon dioxide 42 may be converted into a liquid or a compressed gas and may be recovered from $CO_2$ capture 40 by any suitable method known in the art.

In another embodiment, $CO_2$ capture 40 may be carried out using a conventional acid gas removal system based on aqueous methanolamine (MEA), diethanolamine (DEA), methyldiethanolamine (MDEA), and the like. In a particular embodiment, the $CO_2$ recovery process is done by a Fluor Econamine Process. The Fluor Econamine Process uses MEA coupled with proprietary stabilizer additives, to recover $CO_2$ from various combustion sources, i.e. gas-fired systems. The process is widely used in the oil and gas industry to condition natural gas by removing $CO_2$ from natural gas prior to injection of the processed gas for pipeline delivery. Exemplary suppliers for $CO_2$ recovery systems using an amine process include UOP of Des Plaines, Ill., Shell Global Solutions, and BASF. Typically, the $CO_2$ recovery systems are optimized to process high pressure gas streams found in refining operations. Other solvents used to capture $CO_2$ include the hot potassium carbonate. Mitsubishi provides yet another embodiment of solvent capture using a more complex amine, labeling their product KS-1. Further numerous other processes for the recovery of carbon dioxide are known, see e.g. Herzog et al.,*Annual Review of Energy and the Environment*, vol. 21: 145-166 (November 1996), Carbon Dioxide Recovery and Disposal from Large Energy Systems, U.S. Published Patent Application Nos. 20080072752, 20080060346, and U.S. Pat. Nos. 6,838,071, and 4,810,266.

Figure 5:
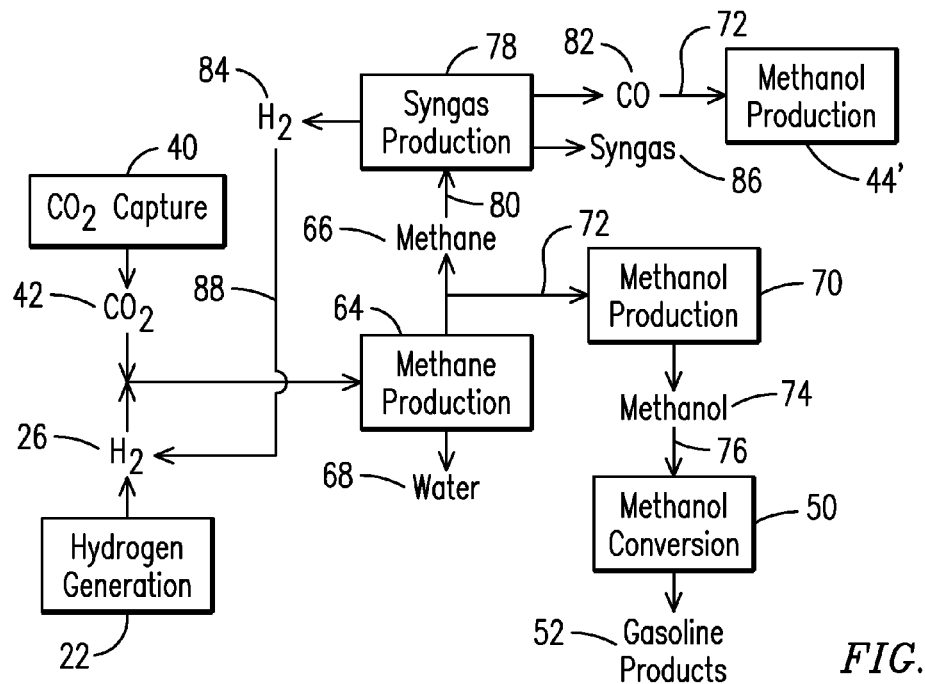
FIG. 5 is a flow schematic of a system for producing carbon dioxide, methane, methanol and/or hydrocarbon fuels from waste carbon dioxide and hydrogen produced from a renewable energy resource according to yet another embodiment of the present invention.

In an embodiment, at least a portion of the hydrogen 26 from hydrogen generation 22 and the carbon dioxide 42 from $CO_2$ capture 40 may be reacted to produce methanol as shown in FIG. 1 (or methane as shown in FIG. 5) according to any suitable process known in the art. In a particular embodiment shown in FIG. 1, at methanol production 44, at least a portion of the hydrogen 26 and the carbon dioxide 42 are reacted to produce methanol 46 according to the one of the following formulas:

$$CO_2 + 2H_2 \rightarrow CH_3OH + \tfrac{1}{2}O_2 \quad \Delta G = -4.1 \text{ Kcal/mole} \qquad (II)$$

Reaction (II) is an electrochemical reaction and may require electricity 18 to drive the reaction. In another embodiment, as shown in FIG. 1, methanol 46 and water 48 are produced at methanol production 44 according to the following equation.

$$CO_2 + 3H_2 \rightarrow CH_3OH + H_2O \qquad (III)$$

Reaction (III) is a well-known reaction in the art typically carried out at 50-350 bar at 250-400° C. over a catalyst, such as a Cu/ZnO catalyst.

As shown in FIG. 5 and discussed in further detail below, the hydrogen 26 and the carbon dioxide 42 may instead be reacted to produce methane and water according to the following formula.

$$CO_2 + 4H_2 \rightleftharpoons CH_4 + 2H_2O \quad \Delta = -27 \text{ Kcal/mole}$$

Generally, the production of methanol is a preferred route because as a liquid it is more readily stored than gaseous products, and methanol is an excellent starting material to produce other chemical commodities (it could for example be a feedstock in Haldor Topsoe's process to make gasoline from methanol). However, the reaction can be tailored to produce either outcome.

The produced methanol 46 may thereafter be directed to a suitable area for storage (not shown) or may be immediately directed to a location for reaction with additional components for the production of addition fuel materials. In one embodiment at least a portion of the produced methanol 46 is further utilized to produce useful hydrocarbon fuel materials. One particularly suitable process for the conversion of the methanol 46 to a useful fuel material is the well-known MTG (methanol to gasoline) process by Exxon Mobil that converts methanol into highly aromatic gasoline products U.S. Pat. Nos. 5,167,937 and 5,026,934 provide examples of processes for the conversion of methanol to useful gasoline products. Thus, in one embodiment, the methanol 46 is directed to methanol conversion 50 as shown by arrow 49 where the methanol 46 is converted into gasoline products 52 using the MTG process as shown by arrow 54. Alternatively, the methanol 46 may be utilized in the production of biodiesel fuels or utilized in a methanol to olefin (MTO) process as is known in the art for the conversion of methanol into ethylene and propylene. Ethylene and propylene are the two largest chemicals produced by the petrochemical industry. The water 48 produced by the reaction of formula (II) may be directed back to a suitable storage facility, utilized in another process as described herein, such as syngas production 78, or may be directed to other any suitable location.

In another embodiment, the recovered carbon dioxide 42 may instead be completely or partially utilized to produce methanol by another reaction that principally requires carbon monoxide, but also requires the presence of the carbon dioxide 42 at methanol production 44'. The reaction takes place according to the formula.

$$CO+2H_2 \rightarrow CH_3OH \qquad (IV)$$

Reaction (IV) is a well-known reaction in the art typically carried out at 50-350 bar at 250-400° C. over a catalyst, such as a Cu/ZnO catalyst.

Figure 2:
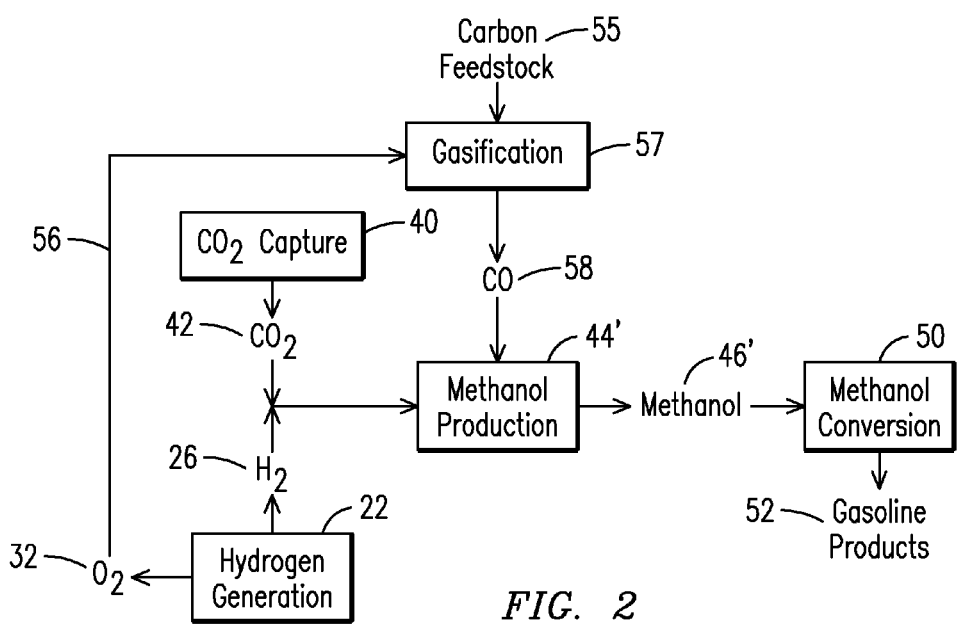
FIG. 2 is a flow schematic of a system for producing methanol and/or hydrocarbon fuels from recovered carbon dioxide and hydrogen produced from a renewable energy resource according to another embodiment of the present invention.

As shown in FIG. 2, the hydrogen 26 from hydrogen generation 22 is combined with carbon monoxide 58 in the presence of the carbon dioxide 42 from $CO_2$ capture 40 to produce methanol 46' at methanol production 44'. Alternatively, the hydrogen for the reaction of formula (IV) may be provided in whole or in part from hydrogen 84 from syngas production 78 as set forth below or from any other suitable hydrogen source.

Figure 3:
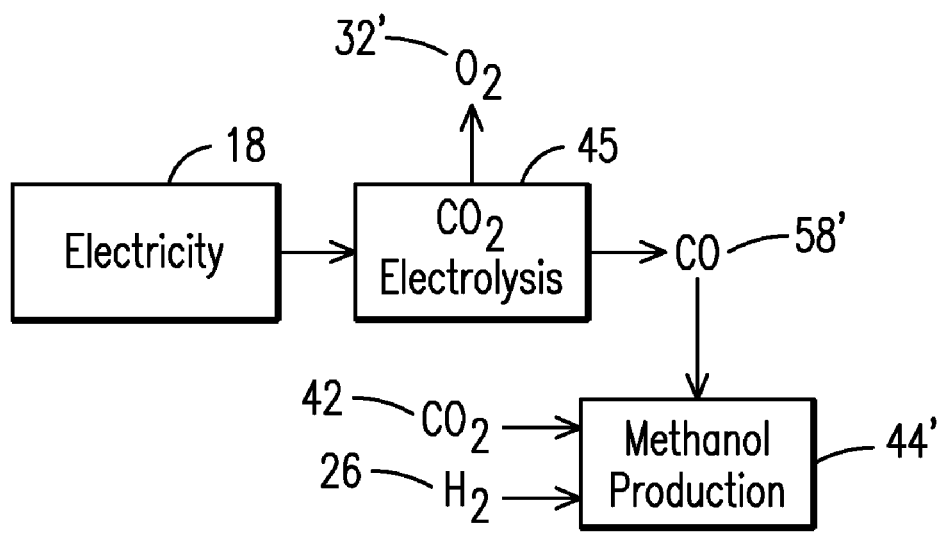
FIG. 3 is a flow schematic of a system for producing methanol, from recovered carbon dioxide, carbon monoxide generated by electrolysis, and hydrogen produced from a renewable energy resource according to yet another embodiment of the present invention.
Figure 4:
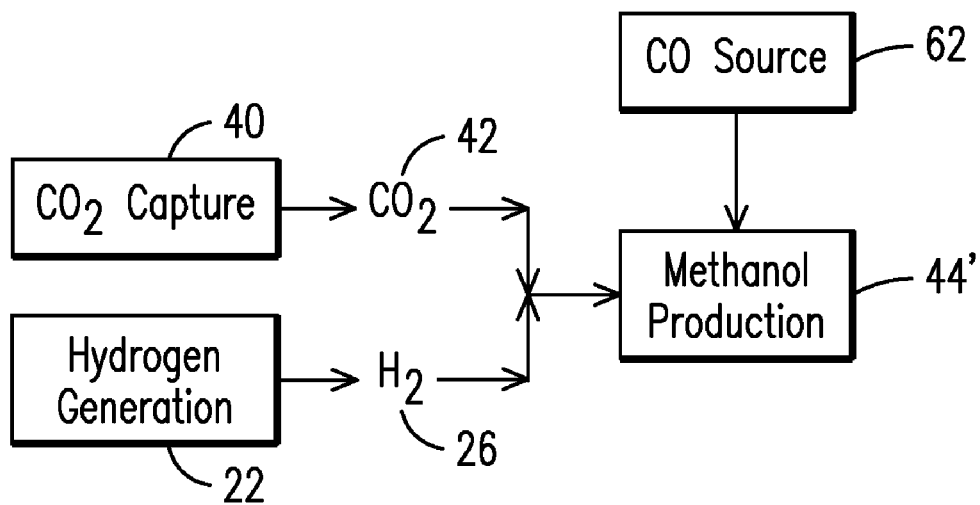
FIG. 4 is a flow schematic of a system for producing methanol from waste carbon dioxide, carbon monoxide, and hydrogen produced from a renewable energy resource according to yet another embodiment of the present invention.

As shown in FIGS. 2-4, the carbon monoxide for the reaction of formula (IV) may be provided from a gasification process (gasification 57), the electrolysis of carbon dioxide ($CO_2$ electrolysis 45), or from an independent carbon monoxide source (CO source 62) as set forth below, or any other suitable source. As shown in FIG. 2, in one embodiment, the carbon monoxide 58 is provided for methanol production 44' by combining the oxygen 32 from hydrogen regeneration 22 (shown by delivered by arrow 56) with a carbon feedstock 55 at gasification 57 according to the following reaction to produce the carbon monoxide.

$$C+\tfrac{1}{2}O_2 \rightarrow CO \qquad (V)$$

In general, nearly all carbon feedstocks have some moisture or other inert/undesirable components. Thus, it is understood that the product gases may not be limited to carbon monoxide as shown above, but could include parallel reactions that produce carbon dioxide, hydrogen, and possibly some water. In one embodiment, to thus limit the number of undesirable products, the feedstock may be delivered (pumped) as a dry product to primarily produce carbon monoxide. A gasifier that is fed with a slurry (liquid, i.e. water, +feedstock) typically has more carbon dioxide (i.e. 10% or so) than one that is fed as a dry feed. Reaction conditions may vary depending upon the feedstock composition, and are typically adiabatic reactor conditions, i.e. 1300° C. to 1,500° C. In another embodiment, however, other products may be formed. For example, carbon monoxide and hydrogen may be produced from a feedstock according to a gasification reaction as set forth in U.S. Pat. No. 5,149,464. In another embodiment, the reaction includes the catalytic partial oxidation of hydrocarbons that are liquid under conditions of standard temperature and pressure to produce hydrogen and carbon monoxide as set forth in U.S. Pat. No. 6,673,270, for example.

Suitable carbon feedstocks include petroleum coke, residual or heavy oil, or other coal materials. Alternatively, the carbon feedstocks may include material having a relatively high carbon content (i.e. 85% or greater). The aim of using a carbon feedstock is to capture the energy value of the low quality feedstock and convert it to a gas stream that can then be converted to a range of high quality products/commodities. In another embodiment, as shown in FIG. 3, the electricity 18 provided at wind farm 12 is used for the electrochemical reduction of the carbon dioxide 42 at $CO_2$ electrolysis 45 according to the following formula to provide another source of carbon monoxide 58'. The electrochemical reaction may be performed in a suitable electrochemical cell.

$$CO_2 \rightarrow CO + \tfrac{1}{2}O_2 \qquad (VI)$$

The carbon dioxide 42 may be provided from $CO_2$ capture 40 or any other suitable source. The resulting carbon monoxide 58' (or mixture of carbon monoxide and carbon dioxide) from $CO_2$ electrolysis 45 may be utilized in the production of methanol 46' at methanol production 44' according to formula (IV). Further, in this embodiment, the oxygen 32' produced according to formula (VI) may also optionally provide an oxygen supply for the reaction of formula (V) at gasification 57 as shown in FIG. 2. In addition, the highly pure oxygen 32 produced by hydrogen generation 22 and the oxygen 32' produced by gasification 57 may be used in any other known gasification technology to provide additional CO that can be used to catalytically convert CO and $H_2$ into chemical products (i.e. methanol) pursuant to formulas (II) and (IV), for example.

In yet another embodiment, as shown in FIG. 4, carbon monoxide 58" may be supplied for the reaction of formula (IV) from any other suitable carbon monoxide source 62 remote from methanol production 44', such as storage tanks or the like to supplement or provide carbon monoxide for methanol production.

It is thus contemplated that the carbon monoxide for the reaction of formula (IV) may come from any one, two, or three sources described above. Typically, the carbon monoxide provided (58, 58', and/or 58") and the hydrogen 26 are reacted on a catalyst, such as a mixture of copper, zinc oxide, and alumina in the presence of added carbon dioxide. The reaction may take place at 5-10 MPa (50-100 atm) and at a temperature of about 250° C. to produce the methanol 46' with high selectivity. The produced methanol 46, may be used for any suitable purpose or may be used to produce gasoline products 52 as described above according to the MTG process.

In another embodiment, as shown in FIG. 5, the recovered carbon dioxide 42 from carbon dioxide capture 40 and the hydrogen 24 from hydrogen generation 22 may be reacted according to the Sabatier process as is known in the art at methane production 64. The resulting products are methane 66, which may be converted to one or more usable hydrocarbon compounds, and water 68, which may be used for any suitable purpose. The Sabatier reaction takes place according to the formula:

$$CO_2 + 4H_2 \leftarrow \rightarrow CH_4 + 2H_2O \Delta = -27 \text{ Kcal/mole} \qquad (VII)$$

The reaction typically takes place at elevated temperatures in the presence of a nickel catalyst. Typically, the reaction takes place at a maximum temperature of about 300° C., although the catalyst selection can reduce the process conditions closer to ambient. U.S. Pat. No. 4,847,231 describes the use of catalysts, i.e. ruthenium, to produce gas phase methane from hydrogen and carbon dixiode, for example. In one embodiment, the produced methane 66 is directed to methanol production 70 as shown by arrow 72 for the conversion of the methane 66 to methanol 74 according to any suitable process for converting methane to methanol known in the art. Currently, approximately 90% of the world's methanol is manufactured from methane. The process is typically accompanied by the partial oxidation of the methane to CO and $H_2$, and then reaction of over a copper catalyst to generate methanol. Currently, the process is available from Haldor Topsoe A/S, Lyngby, Denmark or Davy Process Technology, London, UK. The produced methanol 74 may be directed to methanol conversion 50 as shown by arrow 76 to produce useful gasoline products 52, such as via the MTG process. In another embodiment, the methane 66 is directed to syngas production 78 as shown by arrow 80 and is converted to carbon monoxide 82, hydrogen 84, and/or syngas 86 (a mixture of CO and $H_2$) according to the following reaction.

$$CH_4 + H_2O \rightarrow CO + 3H_2 \qquad (VIII)$$

As set forth in U.S. Pat. No. 6,293,979, the above reaction converting methane to syngas nickel may take place over catalysts, particularly nickel (with or without other elements) supported on alumina or other refractory materials. See Kirk and Othmer, Encyclopedia of Chemical Technology, 3rd Ed., 1990, vol. 12, p. 951; Ullmann's Encyclopedia of Industrial Chemistry, 5th Ed., 1989, vol. A12, pp. 186 and 202; U.S. Pat. Nos. 2,942,958, 4,877,550, 4,888,131, EP 0 084 273 A2; EP 0 303 438 A2; and Dissanayske et al., Journal of Catalysis, vol. 132, p. 117 (1991).

The resulting carbon monoxide 82, hydrogen 84, and syngas 86 may be utilized as desired. For example, the carbon monoxide 82 and the hydrogen 84 may be directed to methanol production 44' as shown by arrow 85 and utilized to produce methanol according to formula (III) above with or without carbon monoxide 58 provided from the carbon monoxide source 62. In addition, the produced hydrogen 84 may be utilized to supplement the hydrogen 26 produced by hydrogen generation 22 as shown by arrow 88 in FIG. 6. Further, either the hydrogen 26 produced by hydrogen generation 22 and the hydrogen 84 from syngas production 78 may be utilized for the production of methanol 44' as set forth in formula (IV).

Figure 6:
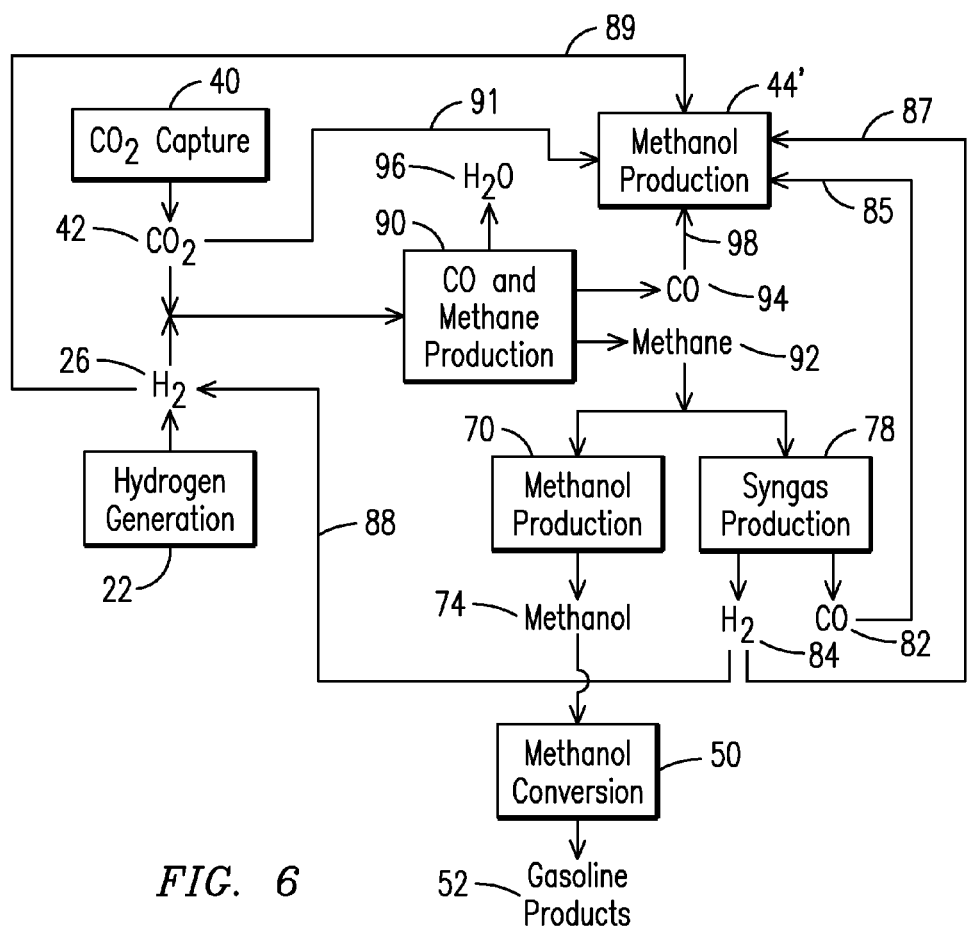
FIG. 6 is a flow schematic of a system for producing carbon dioxide, methane, methanol and/or hydrocarbon fuels from waste carbon dioxide and hydrogen produced from a renewable energy resource according to still another embodiment of the present invention.

In another embodiment, as shown in FIG. 6, at carbon monoxide and methane production 90, the hydrogen 26 and the recovered carbon dioxide 42 may be utilized in a modified Sabatier process in combination with a reverse water gas-shift reaction to produce methane 92, carbon monoxide 94, and water 96 according to the formula:

$$3CO_2 + 6H_2 \rightarrow CH_4 + 2CO + 4H_2O \qquad (IX)$$

For the above reaction, temperatures may range from about 180° C. to about 200° C. and pressures may range from about 50 to about 100 bar over a catalyst. It is contemplated that these values may be higher or lower depending upon the choice of catalyst for the reaction. The hydrogen for the above reaction may also be provided from a downstream process, such as syngas production 78, as discussed below.

The produced methane 92 may be utilized to produce methanol 74 at methanol production 70 and/or converted to syngas and its components, carbon monoxide 82 and hydrogen 84, at syngas production 78. Once the methane 92 is converted to methanol 74 at methanol production 70, the methanol 74 may thereafter be converted to into useful gasoline products 52 at methanol conversion 50 using the MTG process as set forth above. The produced carbon monoxide 94 may be directed to methanol production 44' as shown by arrow 98. Further, the methane 92 may optionally be directed to syngas production 78 and/or methanol production 70. If the methane 92 is directed to syngas production 78, the produced carbon monoxide 82 may be directed to and utilized at methanol production 44'. The amount of produced carbon monoxide 82, 94 may be sufficient to form methanol 46' at methanol production 44' or may supplement the carbon monoxide 58, 58', 58, supplied from other sources. Similarly, the produced hydrogen 84 may be utilized to partially or completely supplement the hydrogen 26 produced by hydrogen generation 22 as shown by arrow 88 for any process described herein. For example, the produced hydrogen 84 may be utilized at methanol production 44' as shown by arrow 87 in lieu of or along with the hydrogen 26 from hydrogen generation 22 (shown by arrow 89), Carbon dioxide for methanol production 44' may be provided from $CO_2$ recovery 40 as shown by arrow 91.

As described above, the present invention provides a relatively inexpensive and optimized system and method for producing useful fuel products from hydrogen generated from renewable energy resources and carbon dioxide provided in waste streams of industrial processes. According to one aspect of the present invention, the carbon dioxide from the waste streams of industrial processes are useful to provide reactants for the production of a number of different fuel materials or are useful as fuel materials themselves. Additionally, instead of being required to dispose of the carbon dioxide from waste streams by costly methods such as deep well injection, the carbon dioxide in the present invention may be utilized to provide sources of methane, methanol, syngas, carbon monoxide, hydrogen, and other hydrocarbon fuel materials, i.e. straight-chain and aromatic hydrocarbons and olefins. In addition, by reacting the carbon dioxide with other compounds, the carbon dioxide may be provided in chemical forms more suitable for storage and transport.

While various embodiments of the present invention have been shown and described herein, it will be obvious that such embodiments are provided by way of example only. Numerous variations, changes and substitutions may be made without departing from the invention herein, Accordingly, it is intended that the invention be limited only by the spirit and scope of the appended claims.

What is claimed is:

1. A process for utilizing CO2 waste comprising:
   recovering carbon dioxide from an industrial process that produces a waste stream comprising carbon dioxide in an amount greater than an amount of carbon dioxide present in starting materials for the industrial process;
   producing hydrogen using a renewable energy resource; and
   producing methane utilizing the produced hydrogen and the recovered carbon dioxide.

2. The process of claim 1, wherein the producing hydrogen is done by electrolysis of water using electricity generated from the renewable energy resource, and wherein the renewable energy resource comprises wind or solar energy.

3. The process of claim 1, wherein the producing hydrogen further comprises producing oxygen as a by-product and using the oxygen in a downstream process.

4. The process of claim 1, further comprising using electricity produced from the renewable energy resource to reduce an amount of carbon dioxide to a first amount of carbon monoxide and oxygen.

5. The process of claim 4, wherein the oxygen is utilized in the gasification of a carbon feedstock to produce a second amount of carbon monoxide, and wherein the second amount of carbon monoxide is utilized in a downstream process.

6. The process of claim 5, wherein at least one of the first amount or the second amount of the carbon monoxide and the produced hydrogen are converted to methanol via a catalytic process.

7. The process of claim 1, wherein the waste stream comprises an exhaust gas from a gas turbine engine.

8. The process of claim 4, further comprising reacting the produced hydrogen with the first amount of carbon monoxide in the presence of the recovered carbon dioxide to produce methanol.

9. The process of claim 1, further comprising converting the produced methane into methanol.

10. The process of claim 1, wherein the produced methane is thereafter converted into syngas.

11. The process of claim 1, further comprising converting the produced methane into carbon monoxide and a second hydrogen supply, wherein the carbon monoxide is directed for use in the production of methanol, and wherein the methanol is produced by reacting the carbon monoxide and at least one of the produced hydrogen from the renewable energy resource and the second hydrogen supply in the presence of the recovered carbon dioxide.

12. The process of claim 1, further comprising converting the produced methane into hydrogen and carbon monoxide and using the hydrogen and the carbon monoxide to produce methanol.

\* \* \* \* \*